United States Patent [19]
Hoetzel et al.

[11] Patent Number: 5,595,647
[45] Date of Patent: Jan. 21, 1997

[54] METHOD FOR DETERMINING GAS COMPONENTS AND/OR GAS CONCENTRATIONS OF GAS MIXTURE

[75] Inventors: Gerhard Hoetzel, Stuttgart; Harald Neumann, Vaihingen; Johann Riegel, Bietigheim-Bissingen, all of Germany

[73] Assignee: Robert Bosch GmbH, Stuttgart, Germany

[21] Appl. No.: 290,703

[22] PCT Filed: Feb. 19, 1994

[86] PCT No.: PCT/DE94/00188

§ 371 Date: Jan. 19, 1995

§ 102(e) Date: Jan. 19, 1995

[87] PCT Pub. No.: WO94/22007

PCT Pub. Date: Sep. 29, 1994

[30] Foreign Application Priority Data

Mar. 19, 1993 [DE] Germany ............. 43 08 767.1

[51] Int. Cl.[6] ................... G01N 27/12; G01N 27/41
[52] U.S. Cl. ................ 205/784.5; 204/424; 204/425; 204/426; 204/427; 422/98
[58] Field of Search ............... 204/153.18, 421–429; 422/98; 205/784.5

[56] References Cited

U.S. PATENT DOCUMENTS 4,272,331  6/1981  Hetrick .
4,416,763  11/1983  Fujishiro ..................... 204/426

FOREIGN PATENT DOCUMENTS 0517366  12/1992  European Pat. Off. .

OTHER PUBLICATIONS

S. Vaihinger et al: "Detection of halogenated and other hydrocarbons in air: Response Functions of Catalyst/Electrochemical Sensor Systems". In: Sensors and Actuators B, vol. 4, 1991 month unavailable, Lausanne CH, pp. 337–343.
J.H. Visser et al: "Sensors for measuring combustibles in the absence of oxygen", In: Sensors and Actuators B, vol. 9, 1992 month unavailable, Lausanne CH, pp. 233–239.
G.J. Maclay: "Use of Time–dependent Chemical Sensor Signals for Selective Identification". In: Sensors and Actuators, 20, 1989 month unavailable, pp. 277–285.
E.M. Logothetis: "Chemical and physical sensors based on oxygen pumping with solid–state electrochemical cells". In: Sensors and Actuators B, 9,1992 month unavailable, pp. 183–189.

*Primary Examiner*—T. Tung
*Attorney, Agent, or Firm*—Spencer & Frank

[57] ABSTRACT

A method of determining at least one of gas constituents and gas concentrations of a gas mixture such as exhaust gas from an internal combustion engine includes producing a change in gas concentration of the gas mixture at a semiconductor gas sensor by pumping a variable supply of oxygen to the semiconductor gas sensor by means of a solid electrolyte pumping cell; detecting at least one reaction speed selected from the group consisting of adsorption speed and desorption speed caused by the change in gas concentration as a signal from the semiconductor gas sensor which is a reply function; evaluating the signal from the semiconductor gas sensor over time to provide a time response of the reply function; and comparing the time response of the reply function with a stored, standardized time response of different gas constituents whereby at least one of the gas constituents and the gas concentrations of the gas mixture are determined.

10 Claims, 1 Drawing Sheet

2

METHOD FOR DETERMINING GAS COMPONENTS AND/OR GAS CONCENTRATIONS OF GAS MIXTURE

BACKGROUND OF THE INVENTION

1. Field of the Invention

The invention is based on a method of determining gas components and/or gas concentrations in gas mixtures, particularly in exhaust gases of internal combustion engines, in which the adsorption and/or desorption speeds of the gas mixture caused by a change in gas concentration at a gas sensor are evaluated.

2. Description of the Related Art

A generic method of determining different gas concentrations of a gas mixture in which the concentration of the gas mixture is modulated in a defined manner in a reaction chamber disposed upstream of a gas sensor is known from Sensors and Actuators, 20 (1989), 277–285. The sensor signal following the modulation is analyzed, and subsequently a conclusion is drawn regarding the corresponding gas components. This method is refined in Sensors and Actuators B, 4 (1991), 337–343 in that a sudden switch between a reference gas and the measured gas has a surging effect on the gas concentration at the gas sensor. A conclusion regarding the gas species is then drawn from the reply function of the sensor signal. In both known methods, the change in the gas mixture concentration takes place in the gas phase, because of which the influenced gas mixture only reaches the sensitive region of the gas sensor by way of a diffusion step. The system thus has a long reaction time. Moreover, the reply function is distorted by the occurring gas diffusion. Finally, the gas diffusion limits the possible frequency spectrum of modulation.

A sensor arrangement for determining CO concentrations, in which an electrochemical oxygen pump cell pumps oxygen to a gas sensor, is also known from Sensors and Actuators B, 9 (1992), 183–189 and 233–239. The gas sensor in this instance is disposed in a measuring chamber without a defined reference to the pump cell and the gas mixture. It is only required that a sufficient oxygen concentration be present at the measuring element. It was determined that the resistance value of an $SnO_2$ gas sensor is three times greater in CO in air with 21% oxygen than in CO in nitrogen.

SUMMARY OF THE INVENTION

The invention makes use of the fact that the different gas species can be characterized by typical adsorption and/or desorption speeds at a gas sensor. The method according to the invention, which has the characterizing features of the main claim, has the advantage that the use of gas sensors with an oxygen cross-sensitivity is possible in selective determination of gas components, for example CO, $NO_x$, HC, with simple means. The gas concentration is directly influenced at the gas sensor by the supply of oxygen, which causes a rapid reaction of the gas sensor to changes in the concentration.

Advantageous refinements and improvements of the method disclosed in the main claim are possible due to the measures outlined in the dependent claims. A particularly realistic time response of the reply function is achieved when the oxygen is supplied to the gas sensor in ion form. Consequently, a surface migration of the oxygen at the sensitive region of the gas sensor can take place significantly faster than by diffusion of the oxygen in the gas phase. A first advantageous embodiment of the method consists of analyzing the transient response of the sensor signal due to an externally-generated, surging change in the gas concentration at the gas sensor. A second advantageous embodiment further consists of evaluating the concentration balance necessary to maintain a constant oxygen concentration at the gas sensor effected by corresponding oxygen supply, using control technology.

BRIEF DESCRIPTION OF THE DRAWINGS

Two embodiments of the invention are described in detail in the following description. The drawing shows, in FIG. 1, a cross-section of a fundamental representation of an embodiment of a sensor system for performing the method of the invention and in FIG. 2, the course of the conductivity σ of an $SnO_2$ semiconductor gas sensor over time.

DESCRIPTION OF THE PREFERRED EMBODIMENTS

Figure 1:
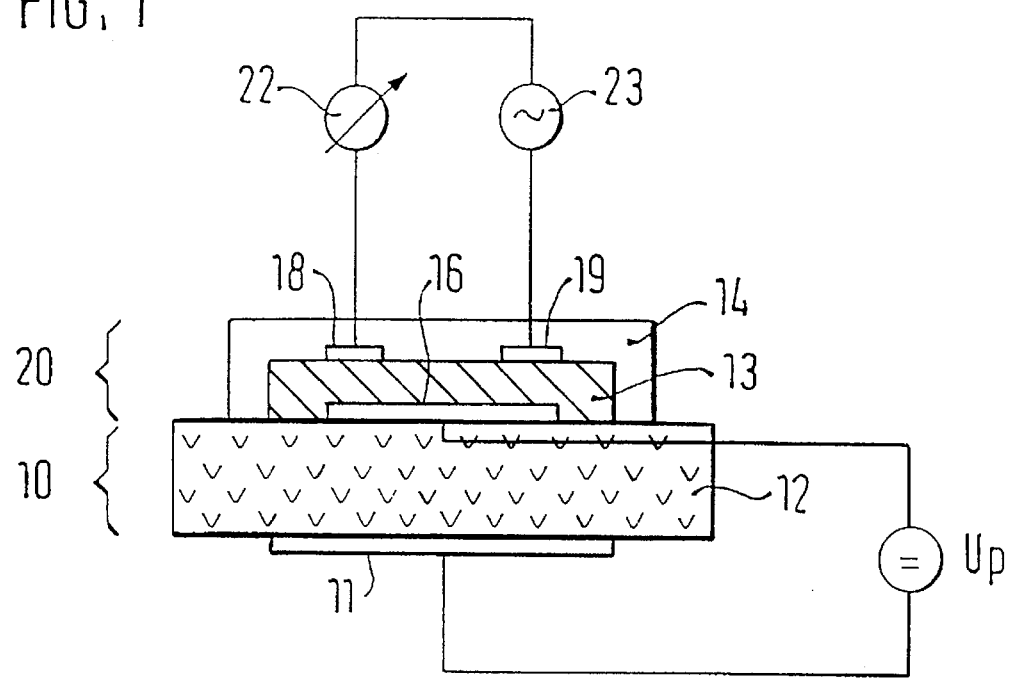

The sensor system illustrated in FIG. 1 has an integrated design comprising an electrochemical oxygen pump cell 10 and a semiconductor gas sensor 20. An outer pump electrode 11 is disposed on the one large surface of a solid electrolyte substrate 12, which is in wafer or film form and comprises an $O_2$ ion-conducting solid electrolyte, for example stabilized zirconium oxide, and an inner pump electrode 16 is disposed on the opposite large surface. The two pump electrodes 11, 16 are made of, for example, platinum or platinum-cermet.

The semiconductor gas sensor 20 includes a first and a second measuring electrode 18 and 19, and a porous, semiconducting metal oxide layer 13. In the present embodiment, $SnO_2$ is used as the semiconducting metal oxide layer. The metal oxide layer 13 is positioned above the inner pump electrode 16 to form the sensitive region. The measuring electrodes 18, 19 are disposed adjacently on the $SnO_2$ layer, at a distance from one another and opposite the inner pump electrode 16. The measuring electrodes 18, 19 and the metal oxide layer 13 are covered by a porous protective layer 14. The porous protective layer 14 can also surround the entire layer system. Furthermore, the sensor system is configured to include a heater, not shown, which is integrated into the layer system.

The application of a d.c. voltage Up to the pump electrodes 11 and 16 causes oxygen to be pumped from the outer pump electrode 11 to the inner pump electrode 16. Either the oxygen to be pumped can be taken from a reference gas present at the outer pump electrode 11 of the pump cell 10, or the sensor is completely submerged in a measured gas in order to pump molecular oxygen or oxygen from oxygen-containing compounds out of the gas mixture by way of the outer pump electrode 11. The measuring electrodes 18, 19 of the semiconductor gas sensor 20 are connected to a measuring voltage source 23 and an ammeter 22. Moreover, a control circuit, not shown, is provided, which is coupled with the pump electrodes 11, 16 and the measuring electrodes 18, 19.

Figure 2:
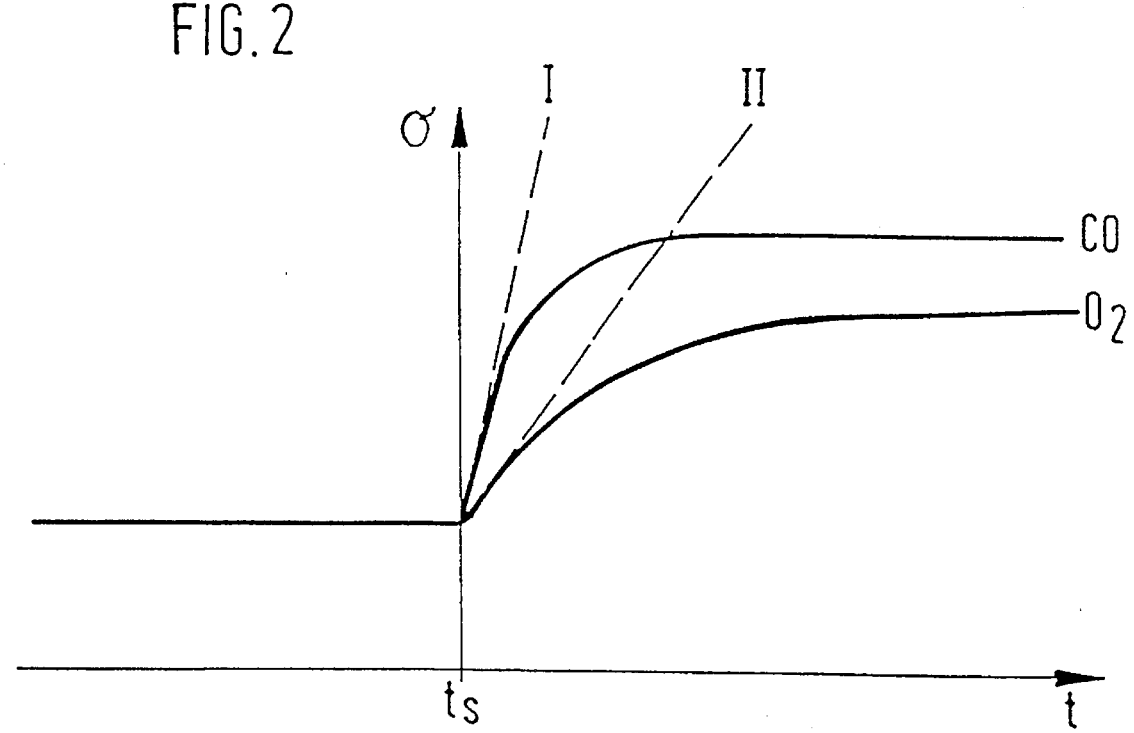

In a first embodiment, the conductivity σ of the gas sensor 20 is measured by means of the ammeter 22, and the conductivity of the gas sensor 20 is controlled so as to reach a constant value by means of the control circuit, through a corresponding setting of the pumping voltage Up (FIG. 2). As can further be seen in FIG. 2, at a time ts the pumping current is shut off, causing the partial pressures in the gas mixture to increase relative to the partial pressure at the sensitive region of the gas sensor 20. In FIG. 2 this increase is represented by the dashed line I for $\Delta pO_2+\Delta pCO$, and for the dashed line II for $\Delta pO_2$. The line I therefore represents the reply function for a gas mixture containing CO, and the line II represents the reply function for a gas mixture exclusively containing $O_2$. The reply functions are fed to a computing system which analyzes the time response and compares the reply function with a standard transient function of individual gas components and gas mixtures, the function being stored in a memory. Different transient functions result because of the different dynamic behaviors of the different gas components and gas mixtures due to the typical adsorption and/or desorption speeds of the gas species, so conclusions can be reached regarding the gas components using them. With increasing time t, the oxygen surplus of the sensitive region is reduced by the reducing effect of the other gas components and the desorption of surplus oxygen at the sensor surface, so a constant conductivity is gradually established. This conductivity value ultimately gives information about the gas concentration of the gas components and/or the gas mixture.

A second embodiment of the method according to the invention is possible in that the conductivity of the gas sensor 20 is evaluated. For this purpose the pumping current and/or the pumping voltage is (are) correspondingly modulated. The time response of the modulation is detracted by means of a frequency response analysis with means of signal analysis that are known per se. For example, a phase-selective rectifier is used for this. The phase shift between pumping current and sensor signal is compared with stored standard values for individual gas components and gas mixtures. As in the first embodiment, the comparison is used to draw conclusions about the gas components. Finally, the amplitude of the modulation frequency gives information about the concentration of the gas components and/or the gas mixture.

The described sensor having an integrated design employs the direct oxygen transfer by way of the spillover effect from the inner pump electrode 16 to the metal oxide layer 13. Because of this heterogeneous catalysis due to the platinum of the electrode 16, a surface migration takes place significantly faster than in a diffusion of the oxygen in the gas phase. In a diffusion in the gas phase, a desorption step of the oxygen from the surface of the pump electrode, as well as an adsorption step of the oxygen at the surface of the metal oxide layer 13, are additionally necessary.

It is also entirely conceivable to implement the method of the invention with sensors in which a porous diffusion layer or a diffusion conduit is provided between the inner pump electrode and the sensitive region. In this type of sensor, however, a longer reaction time must be taken into account because of the transition of the oxygen into the gas phase.

What is claimed is:

1. A method of determining at least one of gas constituents and gas concentrations of a gas mixture such as exhaust gas from an internal combustion engine, comprising:

producing a change in gas concentration of the gas mixture at a semiconductor gas sensor by pumping a variable supply of oxygen to the semiconductor gas sensor by means of a solid electrolyte pumping cell;

detecting at least one reaction speed selected from the group consisting of adsorption speed and desorption speed caused by the change in gas concentration as a signal from the semiconductor gas sensor which is a reply function;

evaluating the signal from the semiconductor gas sensor over time to provide a time response of the reply function; and comparing the time response of the reply function with a stored, standardized time response of different gas constituents whereby at least one of the gas constituents and the gas concentrations of the gas mixture are determined.

2. The method according to claim 1, wherein the variable supply of oxygen is pumped by a solid electrolyte pumping cell which is an electrochemical oxygen pumping cell, wherein the electrochemical oxygen pumping cell converts oxygen to oxygen in ion form by means of a catalysis, and wherein the electrochemical oxygen pumping cell pumps the oxygen in ion form to the gas sensor.

3. The method according to claim 1, wherein the gas concentration of the gas mixture supplied to the gas sensor is changed in a surging manner, and wherein the gas constituents are determined from transient response of the reply function of the sensor signal.

4. The method according to claim 3, wherein the surging change in the concentration of the gas mixture is caused by cutoff of the supply of oxygen.

5. The method according to claim 3, wherein the response function of the signal from the semiconductor sensor has an amplitude, and wherein the amplitude is established by the transient response and is used as a measure of concentration of noxious substances.

6. The method according to claim 1, wherein the signal from the semiconductor gas sensor is modulated by modulation of the variable supply of oxygen at a preselected modulation frequency, and wherein the gas constituents are determined using the time response of the reply function with respect to the preselected modulation frequency.

7. The method according to claim 6, wherein the variable supply of oxygen is pumped by a solid electrolyte pumping cell which is an electrochemical oxygen pumping cell having a pumping current and a pumping voltage, and wherein the signal from the semiconductor gas sensor is modulated by modulation of at least one of the pumping current and the pumping voltage.

8. The method according to claim 6, wherein the modulation frequency has an amplitude, and wherein the amplitude of the modulation frequency is used as a measure of gas concentration.

9. The method according to claim 1, wherein the semiconductor gas sensor has a conductivity, and wherein a preselected oxygen surplus is established at the semiconductor gas sensor to control the conductivity and establish a constant conductivity.

10. The method according to claim 1, wherein the semiconductor gas sensor is an $SnO_2$ gas sensor.

* * * * *